(12) United States Patent
Järvinen et al.

(10) Patent No.: US 7,423,026 B2
(45) Date of Patent: Sep. 9, 2008

(54) METHYLATED CYCLODEXTRIN COMPLEXES

(75) Inventors: Tomi Järvinen, Kuopio (FI); Janne Mannila, Kuopio (FI); Pekka Jarho, Kuopio (FI)

(73) Assignee: PediPharm Oy, Kuopio (FI)

( * ) Notice: Subject to any disclaimer, the term of this patent is extended or adjusted under 35 U.S.C. 154(b) by 506 days.

(21) Appl. No.: 10/505,122

(22) PCT Filed: Feb. 20, 2003

(86) PCT No.: PCT/FI03/00125

§ 371 (c)(1),
(2), (4) Date: Aug. 19, 2004

(87) PCT Pub. No.: WO03/070774

PCT Pub. Date: Aug. 28, 2003

(65) Prior Publication Data

US 2005/0090468 A1 Apr. 28, 2005

(30) Foreign Application Priority Data

Feb. 20, 2002 (FI) .................................. 20020333

(51) Int. Cl.
*A61K 31/05* (2006.01)
*A61K 31/366* (2006.01)
*A61K 31/724* (2006.01)

(52) U.S. Cl. .................... 514/58; 514/454; 514/455; 514/733; 514/738

(58) Field of Classification Search .................... 514/58, 514/455, 738
See application file for complete search history.

(56) References Cited

U.S. PATENT DOCUMENTS

| 4,596,795 A | 6/1986 | Pitha |
| 4,599,327 A | 7/1986 | Nogradi et al. |
| 5,180,716 A | 1/1993 | Yaksh et al. |
| 6,383,513 B1 | 5/2002 | Watts et al. |
| 7,115,586 B2 | 10/2006 | Loftsson |
| 2005/0153931 A1 | 7/2005 | Jarho et al. |

FOREIGN PATENT DOCUMENTS

WO WO-99/32107 A1 7/1999

OTHER PUBLICATIONS

Williamson, E. et al "Cannabinoids in clinical practice" Drugs (2000) vol. 60, No. 6, pp. 1303-1314.*
Hancock, R. "Cationic antimicrobial peptides . . . " Exp. Opin. Invest. Drugs (2000) vik 9, No. 8, pp. 1723-1729.*
Szente, L. et al "Highly soluble cyclodextrin derivatives . . . " Adv. Drug Deliv. Rev. (1999) vol. 36, pp. 17-28.*
Hedges, A. "Industrial applications of cyclodextrins" Chem. Rev. (1998) vol. 98, pp. 2035-2044.*
Kopecky, F. et al "Solubility study of nimodipine inclusion complexation . . . " J. Incl. Phenom. Macr. Phen. (2001) vol. 39, pp. 215-217.*
Worthington, M. et al "Phase solubility analysis in studying the interaction . . . " J. Incl. Phenom. Macr. Phen. (1996) vol. 25, pp. 153-156.*
Y. Shoyama et al., Journal of Natural Products, vol. 46, No. 5, 1983, p. 633-637.
Pekka Jarho et al., Life Sciences, vol. 63, No. 26, 1998, p. 381-384.
David W. Pate et al., Life Sciences, vol. 58, No. 21, 1996, p. 1849-1860.
Pekka Jarho et al., Life Sciences, vol. 58, No. 10, 1996, p. 181-185.
Loftsson et al, *J. Pharm. Sci.*, 85(10):1017-1025 (1996).
Garrett et al, *J. Pharm. Sci.* (Abstract), 63(7):1056-1064 (2006).
Challa et al, "Cyclodextrins in Drug Delivery: An Updated Review", Journal, AAPS-*PharmSciTech*, pp. 1-55, published Oct. 14, 2005.
Pitha et al, *J. Pharm. Sci.* (Abstract), 75(2):165-167 (2006).
Mannila et al, *Eur. J. Pharm. Sci.*, (Article), pp. 1-7, published 2005.
Mannila et al, *J. Pharm. Sci.*, 96(2):312-319 (2007).
Mannilla, Cyclodextrins in Intraoral Delivery of $\Delta^9$-tetrahydrocannabinol and Cannabidiol, Doctroal Dissertation, University of Kuopio (May 11, 2007).
Hazekamp et al, *Eur. J. Pharm. Sci.*, 29:340-347 (2006).
Mannila et al, *Life Sciences*, 78:1911-1914 (2006).
Pitha et al, *J. Pharm. Sci.*, 76(10):788-790 (1987).

* cited by examiner

*Primary Examiner*—Leigh C. Maier
(74) *Attorney, Agent, or Firm*—Birch, Stewart, Kolasch & Birch, LLP

(57) ABSTRACT

The present invention is directed to novel complexes of cyclodextrin. In particular the invention is directed to a complex of a cyclodextrin selected from the group consisting of RM-β-cyclodextrin, DM-β-cyclodextrin and TM-β-cyclodextrin, and a cannabinoid selected from the classical cannabinoid-group consisting of cannabinol, tetrahydrocannabinol and cannabidiol.

20 Claims, 5 Drawing Sheets

METHYLATED CYCLODEXTRIN COMPLEXES

TECHNICAL FIELD OF THE INVENTION

The present invention describes the use of methylated cyclodextrins (CDs) in order to improve the aqueous solubility, dissolution rate and bioavailability of selected cannabinoids, especially classical cannabinoids such as $\Delta^9$-tetrahydrocannabinol (THC). In addition, methylated CDs provide a means to prepare liquid and solid formulations of cannabinoids which can be used in various dosage forms, such as for oral administration, including sublingual and buccal administration, but also nasal and pulmonary administration, parenteral, and topical administration.

BACKGROUND OF THE INVENTION

Cannabinoids are a group of compounds which are ligands to cannabinoid receptors ($CB_1$, $CB_2$) found in the human body (Pertwee, 1997). Cannabinoids were originally found from Cannabis Sativa L., an origin of marijuana and hashish. Over the last few years, marijuana or its components have been reported in scientific literature to counter the symptoms of a broad range of conditions including multiple sclerosis and other forms of muscular spasm, including uterine and bowel cramps; movement disorders; pain, including migraine headache; glaucoma, asthma, inflammation, insomnia, and high blood pressure. There may also be utility for cannabinoids as an oxytoxic, anxiolytic, anti-convulsive, anti-depressant and anti-psychotic agent (Williamson and Evans, 2000), anti-cancer agent, as well as an appetite stimulant.

Nowadays over 60 chemically related compounds, collectively classified as cannabinoids, have been isolated from Cannabis Sativa L., including tetrahydrocannabinol (THC), cannabidiol (CBD) and cannabinol (CBN). In addition, various synthetic ligands for cannabinoid receptors have been developed during the last years. The cannabinoids are usually divided in the groups of classical cannabinoids, non-classical cannabinoids, aminoalkylindol-derivatives and eicosanoids (Pertwee, 1997). Classical cannabinoids are isolated from Cannabis Sativa L. or they can comprise synthetic analogs of these compounds. Non-classical cannabinoids are bi-or tricyclic analogs of tetrahydrocannabinol (THC) (without the pyran ring); aminoalkylindols form a group which differs structurally substantially from classical and non-classical cannabinoids.

The pharmacological and toxicological studies of cannabinoids have been focused mainly on THC (commercially available by the name Dronabinol) which in 1985 was approved by FDA for the treatment of chemotherapy associated nausea and vomiting, and later for AIDS-associated wasting and anorexia. Dronabinol is a synthetic analog of THC which is marketed in USA as Marinol. In Marinol, THC is dissolved in sesame oil and it is administered orally as a capsule containing 5 or 10 mg of THC. The major problem of THC in oral administration is its low bioavailability due to its poor dissolution properties and high first pass metabolism. The bioavailability of orally ingested THC ranges from only 6% to approximately 20% depending on the drug vehicle employed.

Cyclodextrins (CDs) are cyclic oligosaccharides consisting of ($\alpha$-1,4)-inked $\alpha$-D-glucopyranose units, with a lipophilic central cavity and a hydrophilic outer surface (Frömming and Szejtli, 1994). CDs are able to form inclusion complexes with many drugs by taking up the whole drug, or more commonly, the lipophilic moiety of the molecule, into the cavity. The most abundant natural CDs are $\alpha$-cyclodextrin ($\alpha$-CD), $\beta$-cyclodextrin ($\beta$-CD) and $\gamma$-cyclodextrin ($\gamma$-CD), containing six, seven, and eight glucopyranose units, respectively. Of these three CDs, $\beta$-CD appears to be the most useful pharmaceutical complexing agent because of its cavity size, availability, low cost and other properties. Since $\beta$-CD has limited aqueous solubility, numerous water-soluble $\beta$-CD derivatives have been synthesized, including hydroxypropyl-$\beta$-cyclodextrin (HP-$\beta$-CD), sulfobutylether-$\beta$-cyclodextrin (SBE-$\beta$-CD), maltosyl-$\beta$-cyclodextrin (ML-$\beta$-CD) and methylated CDs, including dimethyl-$\beta$-cyclodextrin (DM-$\beta$-CD), trimethyl-$\beta$-cyclodextrin (TM-$\beta$-CD) and randomly methylated $\beta$-cyclodextrin (RM-$\beta$-CD).

In drug formulations, CDs have been used mainly to increase the aqueous solubility, stability and bioavailability of various drugs, food additives and cosmetic ingredients (Frömming and Szejtli, 1994). In addition, CDs can also be used to convert liquid compounds into microcrystalline powders, prevent drug-drug or drug-additive interactions, reduce gastro-intestinal or ocular irritation, and reduce or eliminate unpleasant taste and smell.

Studies dealing with the use of CDs with cannabinoids (classical, non-classical and aminoalkylindol derivatives) are referred to in the following publications. Shoyama et al. (1983) have reported that THC forms an inclusion complex with natural $\beta$-CD with increasing chemical stability of THC. Shoyama et al. (1983) prepared the solid THC/$\beta$-CD inclusion complex by mixing THC and $\beta$-CD in methanol/water solution and hypothesised that CDs may also be used to improve the aqueous solubility and membrane permeability of THC. Jarho et al. (1998) have reported that HP-$\beta$-CD increases the aqueous solubility of THC and co-administration of small amounts of water-soluble polymer (HPMC) enhances the complexation between HP-$\beta$-CD and THC. In addition, Song et al. (2000) and Porcella et al. (2001) have recently used HP-$\beta$-CD to solubilize the aminoalkylindol derivative WIN-55212 in topical ophthalmic formulations.

SUMMARY OF THE INVENTION

The present invention is directed to a novel complex between a specific group of cyclodextrins and cannabinoids. Specifically, the invention relates to a complex of a cyclodextrin selected from the group consisting of RM-$\beta$-cyclodextrin, DM-$\beta$-cyclodextrin and TM-$\beta$-cyclodextrin, and a cannabinoid selected from the classical cannabinoid-group consisting of cannabinol, tetrahydrocannabinol and cannabidiol.

The invention is also directed to a method of preparing such a complex, as well as to pharmaceutical compositions containing such a complex. The complexes or the pharmaceutical compositions containing the same are especially intended for administration through a mucous membrane, such as for sublingual or buccal administration in the form of a tablet, capsule, solution or spray, although also other manners of administration can come into question, such as other oral administration forms, e.g. in the form of tablets and capsules to be swallowed, or in the form of e.g. solutions or solid powders for pulmonary and nasal administration. Also parenteral and topical administration is contemplated, the latter form of administration including the use of the complex for ophthalmic administration.

Furthermore the invention is directed to a method for treating an individual, such as a human, for a condition responsive to treatment with a cannabinoid, the method comprising administering to said individual a sufficient amount of a complex of a cyclodextrin selected from the group consisting of RM-β-cyclodextrin, DM-β-cyclodextrin and TM-β-cyclodextrin, and a cannabinoid selected from the classical cannabinoid-group consisting of cannabinol, tetrahydrocannabinol and cannabidiol.

DETAILED DESCRIPTION OF THE INVENTION

Figure 1:
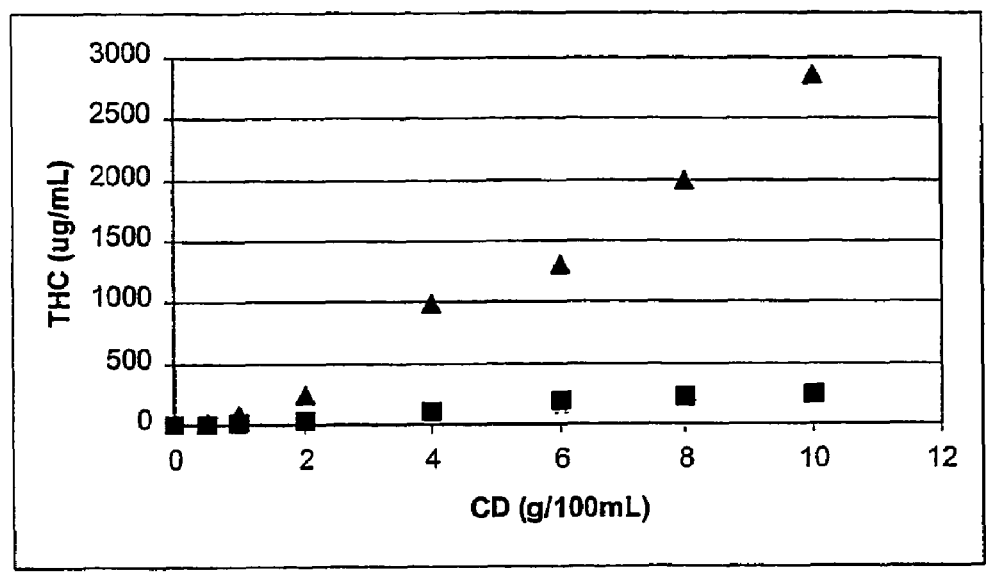
FIG. 1 shows the effect of RM-β-CD (solid triangle) and HP-β-CD (solid square) concentration on aqueous solubility of THC.

The present invention describes the use of methylated CDs to improve the aqueous solubility, dissolution rate, absorption rate and bioavailability of classical cannabinoids.

The present invention is based on the finding that methylated β-CDs increase the aqueous solubility of cannabinoids significantly more compared to other CDs. Thus, high concentrations of cannabinoids in aqueous solution can achieved by the said methylated CDs. By freeze-drying a solution containing the said methylated β-CD and cannabinoid, the cannabinoids can be transformed to a homogenous powder with good dissolution properties. In this powder the cannabinoids are complexed by the CD-molecules (i.e., the cannabinoid molecules are inside of the CD cavity, forming inclusion complexes) the dissolution rate of the cannabinoids increasing due to the excellent solubility/dissolution properties of the CD.

This novel finding can be utilized in a novel type of cannabinoid formulations. Cannabinoids are highly lipophilic compounds with poor dissolution properties. In oral drug delivery the major problem of cannabinoids is a high first-pass metabolism and poor dissolution properties. Thus, sublingual and buccal dosage forms are potential alternatives for cannabinoid therapy due to circumvention of the first-pass metabolism in this manner of administration. The major problem in sublingual and buccal dosage forms is the low aqueous dissolution rate of cannabinoids. In the present innovation the poor dissolution properties have been overcome by means of complex formation with methylated β-CDs that significantly increases the dissolution rate of cannabinoids and allows the use of sublingual and buccal dosage forms of cannabinoids.

The cannabinoid/methylated β-CD complexes can also be utilized in other oral formulations, such as in tablets or capsules, in order to improve the dissolution rate and bioavailability of cannabinoids. In addition, the improved dissolution properties of cannabinoids in CD containing formulations can also be utilized in other drug administration routes of cannabinoids, such as in pulmonary and nasal administration.

Compared to earlier findings, methylated β-CD improves the aqueous solubility of cannabinoids more efficiently, imparting promising dissolution properties for cannabinoids. Jarho et. al. (1998) showed that the aqueous solubility of THC can be increased with HP-β-CD. However, the complexation of cannabinoids with methylated β-CD is more efficient compared to HP-β-CD. This improves the pharmaceutical usefulness of CDs significantly.

As discussed above, the bioavailability of THC is 6-20% after oral administration. THC is commercially available as a capsule containing 5-10 mg of THC (Marinol). Jarho et al. showed that with a 40% solution of HP-β-CD, a 1 mg/ml solution of THC can be obtained. Thus, it can be calculated that 2 g of HP-β-CD is needed to establish a dosage form containing 5 mg of complexed THC. This is an amount that is too much for tablet formulations. According to the invention it has now been shown that the same amount of THC can be complexed with 200 mg of RM-β-CD.

In sublingual and buccal formulations a smaller dose of cannabinoids can be administered due to by-pass of the first pass metabolism. However, also in these applications methylated β-CDs offer superior characteristics compared to, for example, HP-β-CD. As indicated above, for example, 400 mg of HP-β-CD would be needed to complex 1 mg of THC. The same formulation can be prepared with 25.7 mg of RM-β-CD which increases the usefulness of CD technology also in sublingual and buccal drug formulations.

The novel inclusion complexes of the invention can be prepared in conventional manner, known to a person skilled in art. Such complexes are typically made by dissolving a selected cannabinoid in a selected CD. The product is usually a mixture of cannabinoid/CD-complex, uncomplexed cannabinoid and uncomplexed CD. The amounts of cannabinoids and CD are selected to give desired complexation efficiency which also depends on the complexation constant between cannabinoid and CD. The complexation constant ($K_{1:1}$, $K_{1:2}$) between cannabinoids and CDs are usually in a range of 1 $M^{-1}$ to 100 000 $M^{-1}$. Typically cannabinoid and CD are used in a weight ratio (dry weight to dry weight) ranging between 1:4 and 1:1000, such as 1:4 to 1:250. When the methylated CDs are used as a solution such a solution can contain 0.1 to 50% by weight of CD.

The formation of inclusion complex can be facilitated by using solvents, such as organic solvents, for example ethanol. The temperature can vary to some degree, but it is typically for convenience the ambient temperature. Small amounts of water-soluble polymers, such as hydroxypropylmethylcellulose at elevated temperatures can also be used to improve the complexation of cannabinoid with CDs.

After mixing, typically for 1-3 days, the solution obtained is allowed to come to an equilibrium, and can thereafter, if desired, be freeze-dried or spray-dried, to form a powder to be included in a pharmaceutical preparation.

The cannabinoid CD inclusion complexes can also be prepared under heterogenous conditions (suspension) and in solid phase. These methods include methods such as kneading, grinding, and the so-called slurry method. In solution, methods such as co precipitation and neutralization can be used to prepare the solid inclusion complexes.

The pharmaceutical preparation can be any suitable pharmaceutical preparation for oral, including sublingual and buccal, administration, or, for example, for nasal and/or pulmonary administration, but can also be a pharmaceutical preparation for e.g. parenteral, topical or rectal use.

The pharmaceutical preparation according to the invention contains the said complex in pharmaceutically acceptable amounts together with pharmaceutically acceptable carriers, adjuvants or vehicles known in the art. The manufacture of such pharmaceutical formulations is well known in the art.

Thus the pharmaceutical composition may be in a dosage form suitable for oral use, such as tablets, capsules, liquid dosage forms, such as suspensions, emulsions, syrups etc, or e.g. a powder for pulmonary use. All such formulations are made using per se known formulation techniques and carriers, adjuvants and/or additives. Suitable vehicles for making oral administration forms such as tablets or capsules are for example starch, lactose, sucrose, sorbitol, talc, stearates, etc. The complex according to the invention may also be administered parenterally, for example using aqueous or oily suspensions, emulsions, or dispersions containing the active agent in combination with conventional pharmaceutically acceptable excipients. Formulations for rectal use are e.g. suppositories containing the said complex in combination with carrier substances suitable for rectal use.

Also contemplated within the invention is the topical administration of the complex, for which administration form creams, ointments, jellies, solutions, suspensions or the like are useful which contain a pharmacologically active amount of the said complex together with a per se known pharmaceutically acceptable carrier or vehicle.

The therapeutic dose to be given to a patient in need of treatment will vary depending i.a. on the body weight and age of the patient, the particular condition being treated as well as the manner of administration and are easily determined by a person skilled in the art. Generally a concentration of 0.01% to 5% of active agent, cannabinoid, in a suitable carrier would be sufficient for topical use, whereas a dosage form for oral use of 0.1 mg to 5 g, typically 0.1 mg to 500 mg cannabinoid, to be given for example 1 to 4 times a day, would be suitable for most purposes.

The following examples illustrate the invention without limiting the same in any way.

EXAMPLE 1

Figure 2:
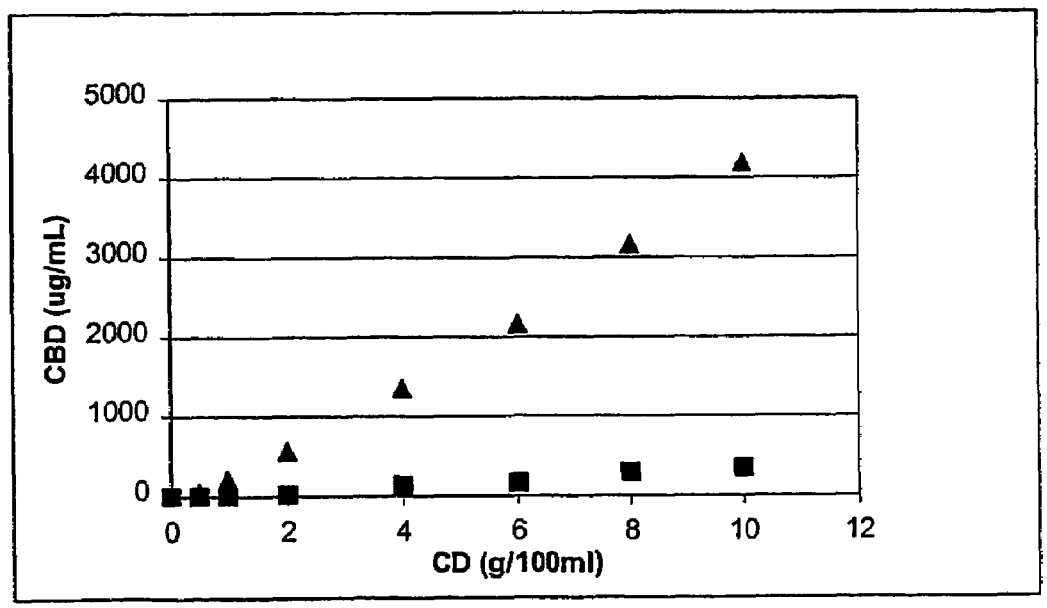
FIG. 2 shows the effect of RM-β-CD (solid triangle) and HP-β-CD (solid square) concentration on aqueous solubility of CBD.

In this example the aqueous solubility studies of THC and CBD with RM-β-CD and HP-β-CD has been shown (FIG. 1. shows the effect of RM-β-CD and (▲) HP-β-CD (■) concentration on aqueous solubility of THC; FIG. 2. shows the effect of RM-β-CD (▲) and HP-β-CD (■) concentration on aqueous solubility of CBD). Solubility studies show that RM-β-CD increases the aqueous solubility of both cannabinoids significantly more compared to HP-β-CD. AU the phase-solubility diagrams (cannabinoid concentration as a function of CD concentration) are Ap-type (Higuchi and Connors 1965) and calculated complexation constants for 1:1 and 1:2 inclusion complexes has been shown in Table 1.

TABLE 1

The calculated complexation constant for 1:1 ($K_{1:1}$) and 1:2 ($K_{1:2}$) inclusion complexes of THC and CBD with RM-β-CD and HP-β-CD, respectively.

| Cannabinoid | CD | $K_{1:1}$ (M$^{-1}$) | $K_{1:2}$ (M$^{-1}$) |
| --- | --- | --- | --- |
| THC | RM-β-CD | 19 563 | 38 |
|  | HP-β-CD | 4 222 | 58 |
| CBD | RM-β-CD | 484 145 | 8 |
|  | HP-β-CD | 13 844 | 62 |

EXAMPLE 2

In this example the effect of RM-β-CD on dissolution characteristics of THC have been shown with four different THC formulations.

The powder containing THC/RM-β-CD inclusion complex was prepared by dissolving CBD in an aqueous RM-β-CD solution which was freeze-dried after equilibration (2 days). The HPLC analysis of powder above showed that 12.4 mg of the powder contained 1.0 mg of THC. All the experiments were performed in 2% RM-β-CD dissolution medias (pH 6.6) to ensure the free dissolution of THC.

Figure 3:
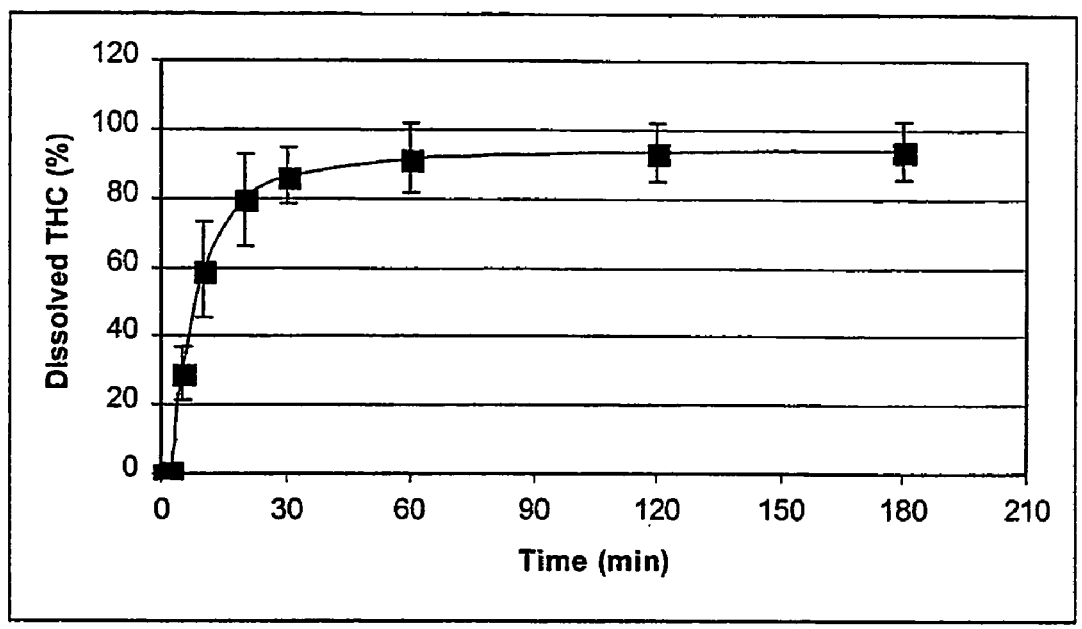
FIG. 3 shows the dissolution profile of THC from a capsule containing 1.0 mg of pure THC and 99 mg of lactose.
Figure 4:
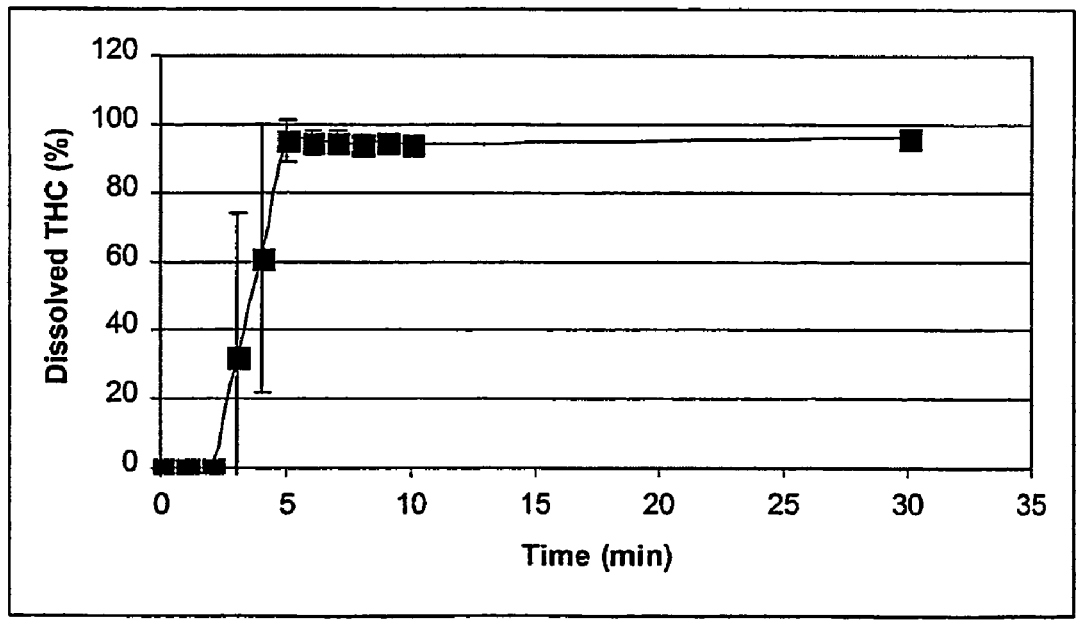
FIG. 4 shows the dissolution profile of THC from a capsule containing 25.7 mg of RM-β-CD/THC-complex and 74.3 mg of lactose.

FIG. 3 shows the dissolution profile (dissolved THC as a function of time) of THC from the gelatine capsule containing 1.0 mg of pure CBD and 99 mg of lactose (Mean ± SD, n=4). FIG. 4 shows the same data with capsule containing 25.7 mg of RM-β-CD/THC-complex (equivalent to 1 mg of THC) and 74.3 mg of lactose (Mean±SD, n=4).

Figure 8:
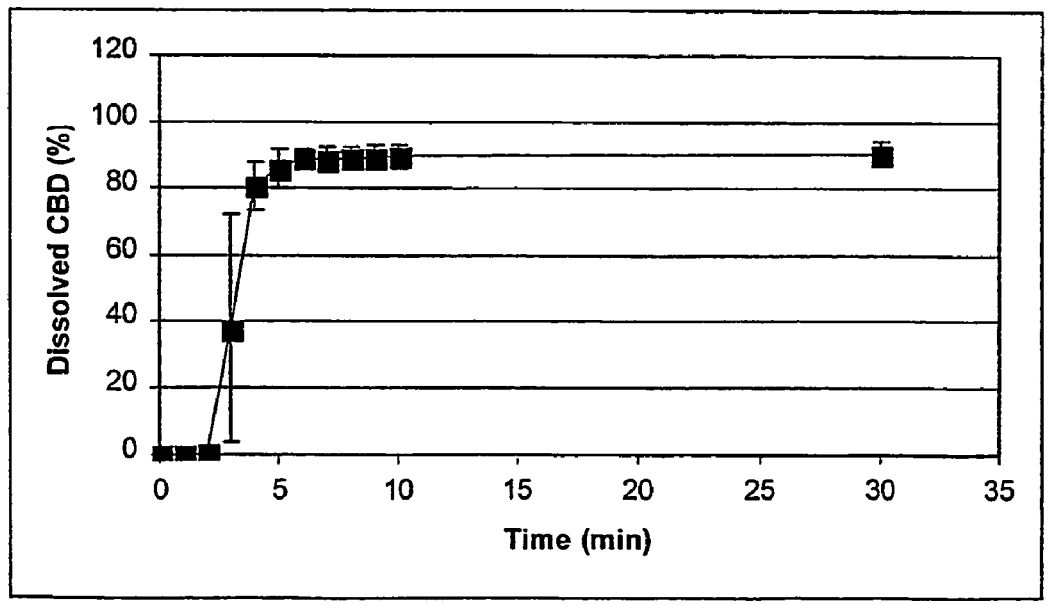
FIG. 8 shows the dissolution profile of CBD from a capsule containing 13.4 mg of RM-β-CD/CBD-complex (equivalent to 1 mg of CBD) and 86.6 mg of lactose.

FIGS. 3 and 4 show that the complexation of THC with RM-β-CD increases significantly the dissolution rate of THC (observe the different time scale in the figures). With RM-β-CD/THC formulation CBDis fully dissolved in 5 minutes and the dissolution of THC is controlled by the dissolution rate of the capsule (FIG. 8). Without RM-β-CD the dissolution rate is much slower and THC is fully dissolved after 1 hour.

Figure 5:
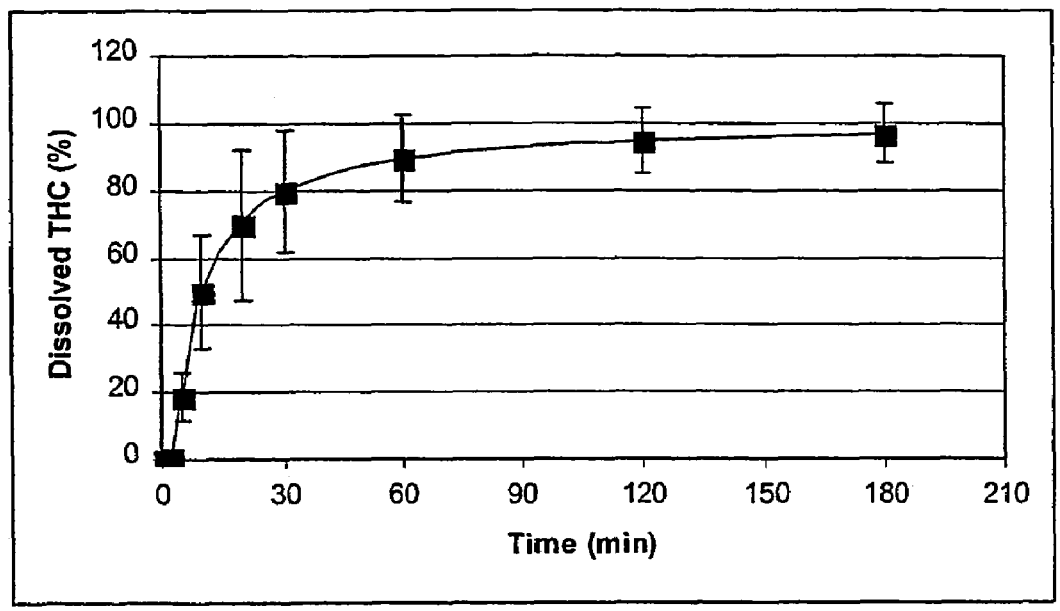
FIG. 5 shows the dissolution profile of THC from a capsule containing a mixture of THC, RM-β-CD and lactose.

In order to study the effect of inclusion complex formation on dissolution of THC the dissolution studies were also performed with the gelatine capsule containing a physical mixture of THC (1.0 mg), RM-β-CD (25.7 mg) and lactose (74.3 mg). The results (FIG. 5, Mean±SD, n=3) show that the physical mixture-formulation did not have an effect on the dissolution rate of THC. Thus, the inclusion complex formation between THC and RM-β-CD is crucial for fast dissolution of THC.

Figure 6:
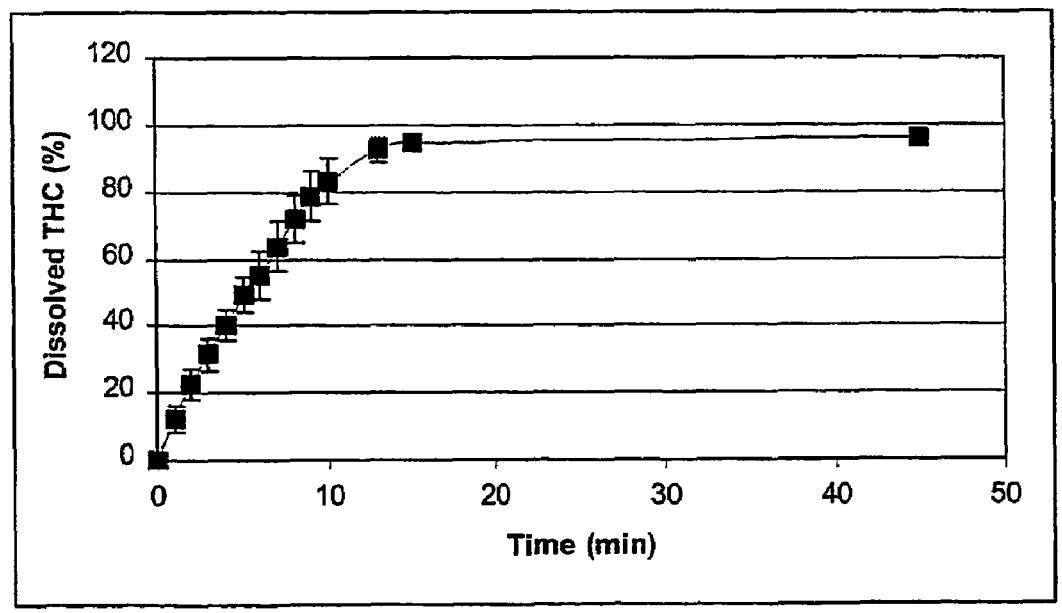
FIG. 6 shows the dissolution profile of THC from a tablet comprising a freeze-dried RM-β-CD/THC-complex.

The dissolution studies were also carried out with the tablet prepared from freeze-dried RM-β-CD/THC-complex. Tablets contained 25.7 mg of RM-β-CD/THC-complex (equivalent to 1.0 mg of THC) power and 74.3 mg of lactose. The results (FIG. 6, Mean±SD, n=6)) show that THC is fully dissolved in 15 minutes, which is significantly faster compared to the gelatine capsule containing pure THC (FIG. 3).

In conclusion, the present results show that the complexation of THC with RM-β-CD increases significantly the dissolution rate of THC.

EXAMPLE 3

In this example the effect of RM-β-CD on dissolution characteristics of CBD have been shown also with four different CBD formulations.

The powder containing CBD/RM-β-CD inclusion complex was prepared by dissolving CBD in the aqueous RM-β-CD solution which was freeze-dried after equilibration (2 days). The HPLC analysis of the powder above showed that 12.4 mg of the powder contained 1.0 mg of CBD. All the experiments were performed in 2% RM-β-CD dissolution medias (pH 6.6) to ensure the free dissolution of CBD.

Figure 7:
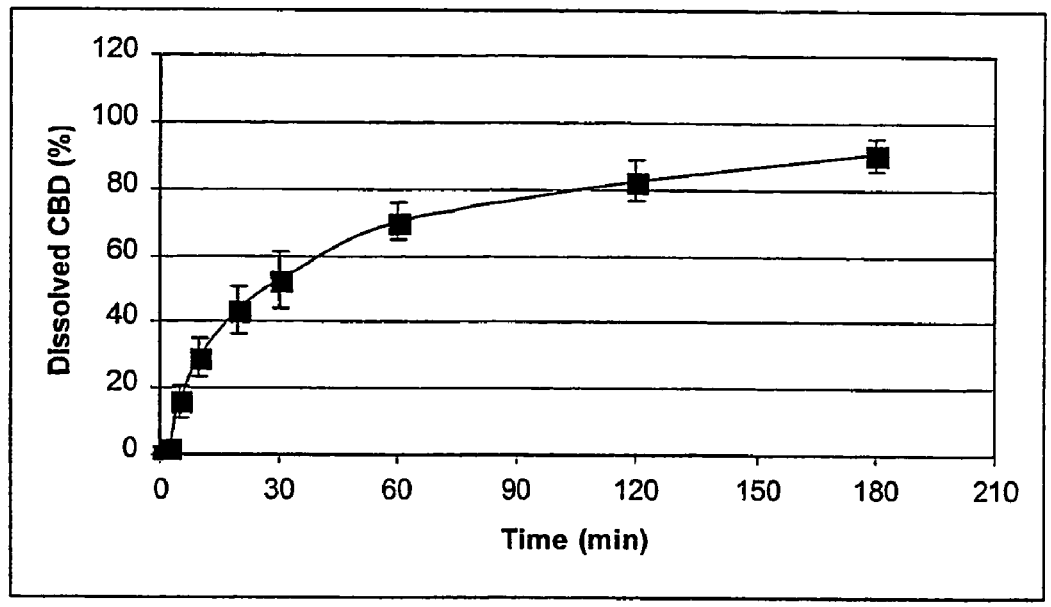
FIG. 7 shows the dissolution profile of CBD from a capsule containing 1.0 mg of pure CBD and 99 mg of lactose.

FIG. 7 shows the dissolution profile (dissolved CBD as a function of time) CBD from the gelatine capsule containing 1.0 mg of pure CBD and 99 mg of lactose (Mean±SD, n=6). FIG. 8 shows the same data with capsule containing 12.4 mg of RM-β-CD/CBD-complex (equivalent to 1 mg of CBD) and 86.6 mg of lactose (Mean±SD, n=6).

FIGS. 7 and 8 show that the complexation of CBD with RM-β-CD increases significantly the dissolution rate of CBD (observe the different time scale in the figures). With RM-β-CD/CBD formulation CBD is fully dissolved in 5 minutes and the dissolution of CBD is controlled by the dissolution rate of the capsule (FIG. 8). Without RM-β-CD the dissolution rate is much slower and CBD is fully dissolved after 3 hours.

Figure 9:
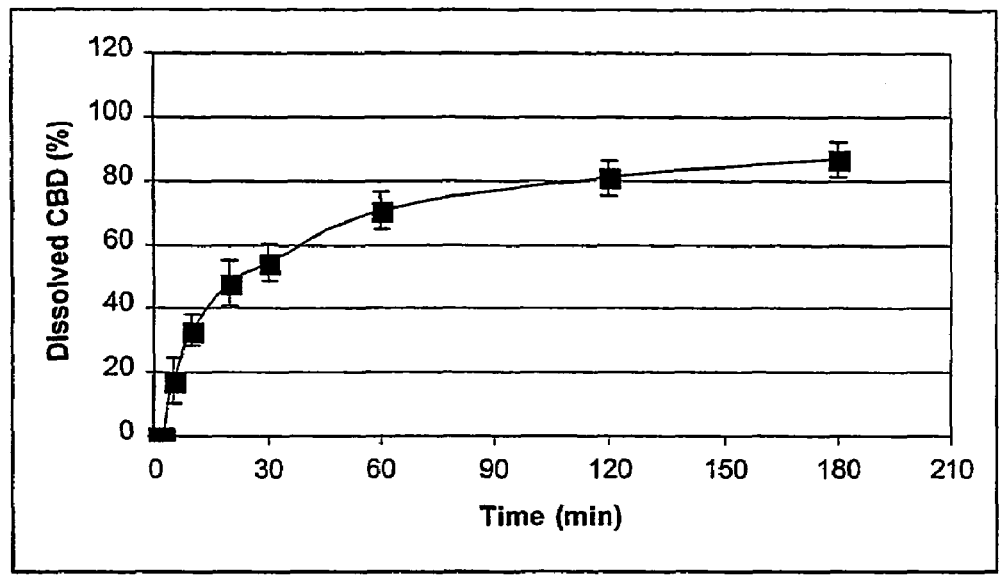
FIG. 9 shows the dissolution profile of CBD from a capsule containing a mixture of CBD, RM-β-CD and lactose.

In order to study the effect of the inclusion complex formation on the fast dissolution of CBD the dissolution studies were also performed with the gelatine capsule containing physical mixture of CBD (1.0 mg), RM-β-CD (12.4 mg) and lactose (86.6 mg). The results (FIG. 9; Mean±SD, n=6) show that physical mixture-formulation did not have an effect on dissolution rate of CBD. Thus, the inclusion complex formation between CBD and RM-β-CD is crucial for the fast dissolution of CBD.

Figure 10:
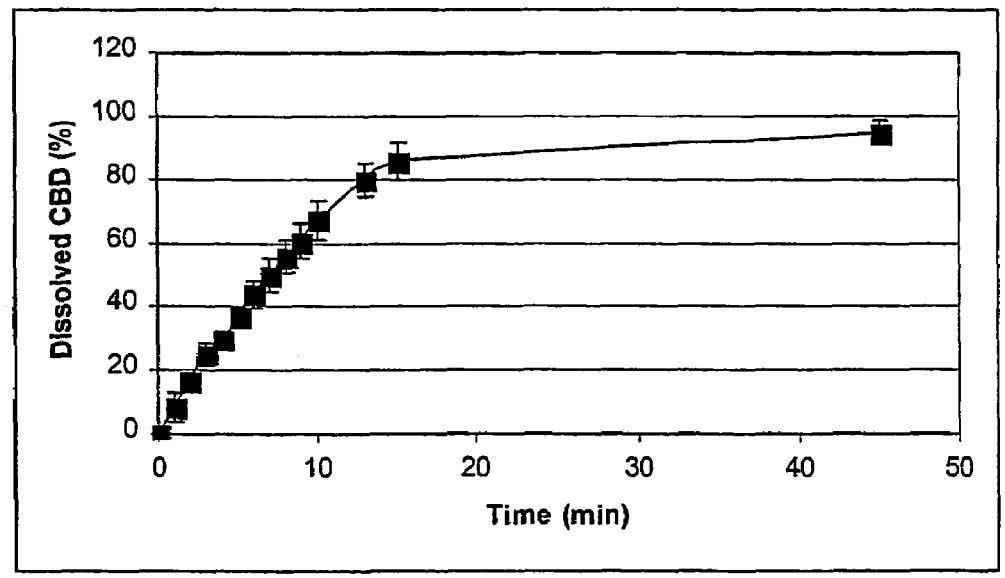
FIG. 10 shows the dissolution profile of CBD from a tablet comprising a freeze-dried RM-β-CD/CBD-complex.

The dissolution studies were also carried out with the tablet prepared from freeze-dried RM-β-CD/CBD-complex. The tablets contained 12.4 mg of RM-β-CD/CBD-complex (equivalent to 1.0 mg of pure CBD) powder and 86.6 mg of lactose. The results (FIG. 10, Mean±SD, n=6) show that CBD is fully dissolved in 15 minutes, which is significantly faster compared to the gelatine capsule containing pure CBD (FIG. 7).

In conclusion the present results show that the complexation of CBD with RM-β-CD increases significantly the dissolution rate of CBD.

REFERENCES

Frömming K-H, Szejtli J: Cyclodextrins in pharmacy. Kluwer Academic Publishers, Dortrecht, 1994.
Higuchi T, Connors K A: Phase-solubility techniques. Adv. Anal. Chem. Instr. 4: 117-212, 1965.
Porcella A, Maxia C, Gessa G L, Pani L: The synthetic cannabinoid WIN55212-2 decreases the intraocular pressure in human glaucoma resistant to conventional therapies. Eur. J. Neurosci. 13: 409412, 2001.
Pertwee, R G: Pharmacology of cannabinoid CB1 and CB2 receptors. Pharmacol. Ther. 74: 129-180, 1997.
Shoyama Y, Morimoto S, Nishioka I: Cannabis XV: preparation and stability $\Delta^9$-tetrahydrocannabinol-β-cyclodextrin inclusion complex. J. Nat. Prod. 46: 633-637, 1983.
Song Z-H, Slowey C-A: Involvement of cannabinoid receptors in the intraocular pressure lowering effects of WIN55212-2. J. Pharm. Exp. Ther. 292: 136-139, 2000.
Williamson E M, Evans F J: Cannabinoids in clinical practise. Drugs 60: 1303-1314, 2000.
Zhang M-Q, Rees D C: A review of recent application of cyclodextrins for drug discovery. Exp. Opin. Ther. Patents. 9:1697-1717, 1999.

The invention claimed is:

1. A complex comprising:
(A) RM-β-cyclodextrin, and
(B) a cannabinoid selected from the group consisting of a tetrahydrocannabinol and a cannabidiol.

2. The complex according to claim 1, wherein the cannabinoid is a tetrahydrocannabinol.

3. The complex according to claim 1, wherein the cannabinoici is $\Delta^9$-tetrahydrocannabinol.

4. The complex according to any one of claims 1, 2, or 3, wherein the cannabinoid and cyclodextrin are present in the complex in a weight ratio, based on dry weight, of 1:4-1:1000.

5. A pharmaceutical composition comprising a therapeutically effective amount of the complex of any one of claims 1, 2, or 3, and at least one pharmaceutically acceptable carrier, adjuvant or additive.

6. The pharmaceutical composition according to claim 5, wherein said composition is an oral dosage composition.

7. The pharmaceutical composition according to claim 6, wherein said composition is in the form of a tablet, a capsule, a solution, a spray or a chewing gum.

8. The pharmaceutical composition according to claim 5, wherein said composition is a pulmonary or nasal dosage composition.

9. The pharmaceutical composition according to claim 8, wherein said composition is in the form of a solution, a spray, or a powder.

10. The pharmaceutical composition according to claim 6, wherein said oral dosage composition is suitable for sublingual or buccal administration.

11. The pharmaceutical composition according to claim 5, wherein said composition is a topical dosage composition.

12. The pharmaceutical composition according to claim 11, wherein said composition is a cream, an ointment, a jelly, a solution, or a suspension.

13. The pharmaceutical composition according to claim 12, wherein said composition comprises 0.01% to 5% of cannabinoid.

14. The complex according to claims 1, 2, or 3 wherein the cannabinoid and cyclodextrin are present in the complex in a weight ratio, based on dry weight, of 1:4-1:250.

15. A method of treatment of a subject comprising administering to a subject afflicted with or suffers from nausea, muscular spasms, multiple sclerosis, uterine cramps, bowel cramps, a movement disorder, pain, migraine headache, glaucoma, asthma, inflammation, insomnia, high blood pressure, cancer, anxiety, convulsions, depression or psychosis, an effective amount of the complex of claim 1, 2, or 3.

16. The method according to claim 15, wherein said complex is administered orally such that from 0.1 to 5 g of cannabinoid are administered per day.

17. The method according to claim 16, wherein said complex is administered orally such that from 0.1 to 500 mg of cannabinoid are administered per day.

18. The method according to claim 15, wherein said complex is topically administered.

19. The method according to claim 18, wherein said complex is in a composition selected from the group consisting of a cream, an ointment, a jelly, a solution, or a suspension.

20. The method according to claim 19, wherein said composition comprises 0.01% to 5% of cannabinoid.

* * * * *